United States Patent [19]

Bright

[11] 4,288,615
[45] Sep. 8, 1981

[54] PROCESS FOR RECOVERING 3-NITROBENZOIC ACID

[75] Inventor: John H. Bright, Kendall Park, N.J.

[73] Assignee: American Cyanamid Company, Stamford, Conn.

[21] Appl. No.: 122,957

[22] Filed: Feb. 21, 1980

[51] Int. Cl.³ .............................................. C07C 51/43
[52] U.S. Cl. ..................................................... 562/434
[58] Field of Search .......................................... 562/434

[56] References Cited

U.S. PATENT DOCUMENTS 3,415,876  12/1968  Boonstra et al. .................... 562/434

*Primary Examiner*—Natalie Trousof
*Assistant Examiner*—Michael Shippen
*Attorney, Agent, or Firm*—Bruce F. Jacobs

[57] ABSTRACT

3-Nitrobenzoic acid is recovered from a mixture of 2-, 3- and 4-nitrobenzoic acids by basifying to a pH of 8–12 and then adding an acid to reduce the pH to 1.5–3.5 to precipitate the desired compound.

10 Claims, No Drawings

PROCESS FOR RECOVERING 3-NITROBENZOIC ACID

This invention pertains to a process for the recovery of 3-nitrobenzoic acid. More particularly, it pertains to an improved process for the separation of 3-nitrobenzoic acid from a mixture of isomeric nitrobenzoic acids.

The nitration of benzoic acid to form 3-nitrobenzoic acid is widely known to give mixtures of 2-, 3-, and 4-nitrobenzoic acids. Recrystallization, usually from water, or a mixture of alcohol and water, gives either unacceptable purity or low yields of the desired 3-nitrobenzoic acid, which is used in the preparation of 3-N,N-dimethylaminobenzoic acid, an intermediate in the preparation of Crystal Violet Lactone, a commercial color former.

British Pat. No. 1,519,602 discloses a process for the preparation of 3-nitrobenzoic acid by nitration of benzoic acid with nitric acid in sulfuric acid below 10° C. over about 2 hours. The mixture is then warmed to 40° C. and diluted with water to precipitate a crude product containing about 9% of the 2-isomer and less than 1% of the 4-isomer. After recrystallization from water, the yield of 3-nitrobenzoic acid was 80% of theoretical.

British Pat. No. 1,519,617 discloses the preparation of 3-nitrobenzoic acid by the nitration of benzoic acid with a mixture of nitric acid, sulfuric acid, and sulfur trioxide at −5° to 30° C. However, this process requires the use of 60% sulfur trioxide in the mixed acid which creates handling and disposal problems requiring special equipment.

Hirata and Goto, Research Reports Nagoya Ind. Sci. Research Inst. No. 6, p 37–38 (1953), (Chemical Abstracts, Vol. 49, 2363g) discloses four methods for the preparation of 3-nitrobenzoic acid. The easiest and most economical process involves the rapid addition of fuming nitric acid to a stirred mixture of benzoic acid in concentrated sulfuric acid until the temperature reaches 80° C., then slowly at the constant temperature. Upon completion of the addition of the fuming nitric acid, the reaction mixture is poured into ice water, filtered, and the recovered crystals are washed with water, heated to 70° C. to liquify, chilled, and vigorously stirred to obtain a 58.7% yield of 3-nitrobenzoic acid, m.p. 140°–141° C.

Netherlands Appln. No. 66-01366 (Chemical Abstract, Vol. 68 95548A) discloses a process for the preparation of 3-nitrobenzoic by adding anhydrous nitric acid to a mixture of benzoic acid and sulfur trioxide. After the addition is completed, the sulfor trioxide is evaporated to obtain a white solid which is recrystallized from a mixture of alcohol and water to obtain pure 3-nitrobenzoic acid, m.p. 141° C.

In accordance with the present invention, a process is provided for the recovery of highly pure 3-nitrobenzoic acid from a mixture of 2-, 3-, and 4-nitrobenzoic acids, dissolving the washed precipitate in an aqueous solution of a suitable base to form a solution having a pH of about 8–12, and adding a suitable acid to the resulting solution to adjust the pH to about 1.5–3.5 and precipitate 3-nitrobenzoic acid; then preferably heating the resulting slurry to about 40°–100° C., preferably about 50°–80° C., cooling the resulting solution to about 0°–30° C., preferably about 20°–30° C., and recovering the precipitated pure 3-nitrobenzoic acid.

In the preferred embodiment, the crude 3-nitrobenzoic acid is first rinsed with water (5°–40° C.) to remove most of the residual inorganic acids therein and dissolved in an aqueous base to form a solution having a pH of about 8.5–10. Then the resulting solution is clarified by filtration. After clarification, the resulting mother liquor is acidified to a pH of about 1.8–3.0, the resulting slurry is heated to about 60°–65° C., and the resulting solution is cooled to about 25° C. before recovering the 3-nitrobenzoic acid.

The process of the present invention is distinguished from the prior art in that it provides excellent recovery of the desired isomer in a high state of purity (97–99%) in a simple solution-precipitation cycle. The recovery is about 95% of theoretical, or higher.

In carrying out the present invention, crude 3-nitrobenzoic acid from the nitration of benzoic acid may be washed with water at 0°–35° C., preferably at 5°–25° C., to remove most of the residual sulfuric acid and any unreacted nitric acid. The water-washed crude precipitate is added to water, about 2.5 to 10 parts by weight of water, preferably about 5–6 parts by weight of water, per part by weight of crude 3-nitrobenzoic acid, and a suitable aqueous base is added thereto to adjust the pH to about 8–12, preferably about 8.5–10. Suitable aqueous bases include ammonium hydroxide, sodium hydroxide, sodium carbonate, potassium hydroxide and the like. Preferably the aqueous base is ammonium hydroxide or sodium hydroxide.

The resulting solution, containing salts of 2-, 3-, and 4-nitrobenzoic acids, may then be clarified by suitable means, preferably by filtration, and the resulting mother liquor is acidified to a pH of about 1.5–3.5, preferably about 1.8–3.0, by adding a suitable acid thereto. This precipitates out the desired 3-nitrobenzoic acid. Suitable acids for this purpose include nitric, hydrochloric, hydrobromic, hydroiodic, sulfuric, chloric, formic, acetic, citric, and the like. The acid chosen must form a salt with the base which is completely soluble in warm (50°–80° C.) water. For example, nitric or hydrobromic acid is preferably used in conjunction with ammonium hydroxide, and acetic or formic acid is preferably used in conjunction with pottassium hydroxide.

Calcium hydroxide may be used in conjunction with hydrochloric acid as the acidifying agent.

In the particularly preferred embodiment, the base is aqueous ammonium hydroxide and the acid is diluted nitric acid.

The resulting slurry may then be heated to about 40°–100° C., preferably about 50°–80° C., most preferably about 60°–65° C., to dissolve any inorganic salts which may have co-precipitated with the 3-nitrobenzoic acid. The solution is then cooled to 0°–30° C., preferably to about 20°–30° C., and the precipitate is recovered to obtain 3-nitrobenzoic acid having a purity of about 98%, which contains about 0.1% by weight of 4-nitrobenzoic acid and less than 0.1% by weight of 2-nitrobenzoic acid. The recovery from the crude precipitate is about 95–99% of theoretical.

The process of this invention is applicable for the purification of 3-nitrobenzoic acid from any source. Preferably, the crude mixture of isomers of nitrobenzoic acid contains a high percentage of the desired 3-nitrobenzoic acid. More preferably, the crude material is prepared using the nitration conditions described in the Examples herein.

The following examples illustrate the processes of the present invention. All parts and percents are by weight unless otherwise indicated.

EXAMPLE 1

A mixture of 22 grams of 70.7% nitric acid (15.6 grams real; 0.25 mole) in oleum (41 grams of 98% sulfuric acid containing 25–30% sulfur trioxide) is added to a stirred solution of benzoic acid (30.5 grams; 0.25 mole) in 83 grams of the aforedescribed oleum over a period of 3 hours while maintaining the temperature of the reaction mixture between 5° and 15° C. After the addition is completed, the reaction mixture is stirred for an additional hour and allowed to warm up to room temperature. The reaction mixture is then poured onto cracked ice (150 grams) to precipitate a crude product consisting mainly of a mixture of 2-, 3-, and 4-mononitrobenzoic acids.

The precipitate is separated and washed with cold (5°–10° C.) water (250 grams) to obtain a washed, crude product. Analysis of a small portion of the wet crude product shows that it contains 64% 3-nitrobenzoic acid, 6% 2-nitrobenzoic acid, and 0.3% 4-nitrobenzoic acid. Based on this analysis, the yield of 3-nitrobenzoic acid is 61%.

The washed, crude product is added to water (225 mls) and the stirred mixture is treated with 29% aqueous ammonium hydroxide (27 mls) to adjust the pH of the mixture to 8.5. The solution is clarified by filtration and then dilute nitric acid (19 grams of 70.7% nitric acid in 39 mls of water) is added to the mother liquor to adjust the pH to 2 and precipitate 3-nitrobenzoic acid.

The resulting slurry is warmed to 60°–65° C. to dissolve any coprecipitated inorganic salts, and cooled to room temperature (25° C.).

The precipitate is separated by filtration and dried to obtain 25 grams of 3-nitrobenzoic acid (97% real), containing less than 0.1% 2-nitrobenzoic acid and 0.1% 4-nitrobenzoic acid. The recovery of 3-nitrobenzoic acid from the crude is 95%.

EXAMPLE 2

The procedure of Example 1 is followed in every detail except that the crude product is washed with 120 mls of cold water. The washed crude is added to water (200 mls) and 5 N sodium hydroxide (109 mls) is added to adjust the pH to 10. The solution is then diluted with water to a total volume of 700 mls and clarified by filtration. The mother liquor is then treated with a dilute solution of nitric acid (50 mls of 10 N nitric acid in 200 mls of water) to adjust the pH to 2 and precipitate the product. The resulting slurry is then processed, as described in Example 1, to obtain 20 grams of product, containing 98% 3-nitrobenzoic acid and less than 0.1% each of 2- and 4-nitrobenzoic acids.

EXAMPLE 3

A mixture of 23.5 grams of 70% nitric acid (16.4 grams real; 0.25 mole) in concentrated sulfuric acid (59 grams of 98% real) is added to a suspension of benzoic acid (30.5 grams; 0.25 mole) in 109 grams of 98% real sulfuric acid over a period of one hour, while maintaining the temperature of the reaction mixture between 28° and 37° C. After the addition is completed, the reaction mixture is stirred for an additional 30 minutes at room temperature, and then poured onto cracked ice (150 grams) to precipitate a crude product, consisting mainly of a mixture of 2-, 3-, and 4-mononitrobenzoic acids, which is subsequently recovered by filtration. The wet, paste-like cake (134 grams) contains the 2-, 3-, and 4-nitrobenzenes in yields 16%, 77% and 1.4%, respectively. The cake is washed with 105 grams of water at 20° C. to obtain 84 grams of wet cake which contains the 2-, 3-, and 4-nitrobenzoic acids in yields of 6%, 77%, and <0.2%, respectively; the isomer ratio is 2.1 to 10 to <0.03, respectively.

The washed cake is added to 100 mls of water and treated with about 110 mls of 5 N aqueous sodium hydroxide to obtain a solution having a pH of about 10. The solution is clarified by filtration, and 5 N nitric acid is added to the mother liquor to adjust the pH to 3.0, and precipitate 3-nitrobenzoic acid. The resulting slurry is heated to 60°–65° C. to dissolve any coprecipitated inorganic salts, cooled to 25° C., and separated by filtration. The resulting cake is then washed with 100 mls of hot (60° C.) water and 300 mls of warm (30° C.) water. The washed cake is then dried to obtain 32.2 grams of 3-nitrobenzoic acid containing 0.23% of 2-nitrobenzoic acid, and less than 0.1% of 4-nitrobenzoic acid. The overall yield of 3-nitrobenzoic acid is 77% of theoretical; the recovery of 3-nitrobenzoic acid from the crude cake is about 100% of theoretical. The isomer ratio of 2-, to 3-, to 4-nitrobenzoic acids is 0.023 to 10 to <0.01.

What is claimed is:

1. A process for the recovery of 3-nitrobenzoic acid from a mixture of 2-, 3-, and 4-nitrobenzoic acids comprising adding to the mixture an aqueous solution of a suitable base to form a solution having a pH of about 8–12, adding a suitable acid to lower the pH to about 1.5–3.5 and precipitate 3-nitrobenzoic acid as a slurry, and recovering said 3-nitrobenzoic acid.

2. The process of claim 1 wherein prior to adding the aqueous base the mixture is rinsed with water to remove residual acids.

3. The process of claim 1 wherein after adding the aqueous base and prior to adding an acid the solution is clarified by filtration.

4. The process of claim 1 wherein after the 3-nitrobenzoic acid has precipitated as a slurry, the slurry is heated to about 40°–100° C. and cooled to about 0°–30° C. before separating the 3-nitrobenzoic acid.

5. The process of claim 1 wherein initially the mixture is rinsed with water at about 5°–25° C., then the aqueous solution of a suitable base is added to form a solution having a pH of about 8–12, then the solution is clarified by filtration, then the suitable acid is added to lower the pH to about 1.5–3.5 and precipitate 3-nitrobenzoic acid as a slurry, then the slurry is heated to about 50°–80° C., and then the slurry is cooled to about 20°–30° C. before separating the 3-nitrobenzoic acid.

6. The process of claim 5 wherein the pH after the addition of the base is about 8.5–10, the pH after the addition of the acid is about 1.8–3, and the slurry is heated to about 60°–65° C.

7. The process of claims 1 or 5 wherein the base is selected from ammonium hydroxide, sodium hydroxide, sodium carbonate and potassium hydroxide.

8. The process of claims 1 or 5 wherein the acid is selected from nitric, hydrochloric, hydrobromic, hydroiodic, sulfuric, chloric, formic, acetic, and citric acids.

9. The process of claims 1 or 5 wherein the base is ammonium hydroxide and the acid is nitric acid or hydrobromic acid.

10. The process of claims 1 or 5 wherein the base is ammonium hydroxide and the acid is dilute nitric acid.

* * * * *